United States Patent [19]
Hazard, Jr.

[11] Patent Number: 5,384,011
[45] Date of Patent: Jan. 24, 1995

[54] PROCESS FOR CROSSLINKING OF CELLULOSIC FIBERS

[75] Inventor: Sherrill J. Hazard, Jr., Appleton, Wis.

[73] Assignee: James River Corporation of Virginia, Richmond, Va.

[21] Appl. No.: 17,037

[22] Filed: Feb. 12, 1993

[51] Int. Cl.⁶ .......................... D21H 11/20
[52] U.S. Cl. ........................ 162/9; 162/17; 162/100; 162/157.6; 162/182; 162/207
[58] Field of Search ............ 162/9, 100, 157.6, 182, 162/17, 207

[56] References Cited

U.S. PATENT DOCUMENTS

| | | | |
|---|---|---|---|
| 3,440,135 | 4/1969 | Chung | 162/157.6 |
| 4,204,055 | 5/1980 | Lesas et al. | 162/157.6 |
| 4,244,778 | 1/1981 | Lindahl et al. | 162/17 |
| 4,822,453 | 4/1989 | Dean et al. | 162/157.6 |
| 4,889,597 | 12/1989 | Bourbon et al. | 162/157.6 |
| 4,911,700 | 3/1990 | Makoui et al. | 162/157.6 |
| 5,137,537 | 8/1992 | Herron et al. | 162/157.6 |
| 5,183,707 | 2/1993 | Herron et al. | 162/157.6 |
| 5,190,563 | 3/1993 | Herron et al. | 162/157.6 |

*Primary Examiner*—Peter Chin

[57] ABSTRACT

An improved process for preparing crosslinked individualized cellulosic fibers wherein drying and curing are carried out in two separate stages while the fibers are entrained in turbulent pressurized superheated steam at elevated temperatures.

16 Claims, 2 Drawing Sheets

PROCESS FOR CROSSLINKING OF CELLULOSIC FIBERS

This invention is concerned with cellulosic fibers exhibiting improved resilient bulking both in the wet and dry states and also with absorbent structures incorporating said cellulosic fibers. More specifically, this invention is concerned with a novel process for producing individualized anfractuous crosslinked cellulosic fibers, where the novelty resides in heating crosslinker treated fibers by entraining them in turbulent superheated steam at particular pressures and temperatures, individualizing said fibers and then curing the fibers while entrained in turbulent superheated steam at elevated temperatures and pressures.

BACKGROUND OF THE INVENTION

Fibers crosslinked in substantially individualized form and various methods of making such fibers have been described in the art. As is known in the art, the term "individualized crosslinked fibers" refers to cellulosic fibers that have primarily intrafiber crosslinked bonds, that is, the crosslinked bonds are primarily between cellulose molecules in a single fiber rather than being between cellulose molecules of separate fibers. Individualized crosslinked fibers are generally regarded as being useful in product applications wherein high bulk, high absorbency or both are desirable. Absorbent structures containing individualized crosslinked fibers generally exhibit an improvement in at least one significant absorbency property relative to conventional uncrosslinked fibers. Structures incorporating these fibers also generally exhibit a high degree of bulk.

A good discussion of the prior art is disclosed in U.S. Pat. No. 5,137,537, the entire disclosure of which is incorporated herein by reference.

As can be seen from said U.S. Pat. No. 5,137,537 and its disclosure of the prior art, there have been many processes for crosslinking individualized cellulosic fibers and a wide variety of crosslinking agents have been used including formaldehyde and addition products known as n-methylol agents or n-methylolamides. Dialdehyde crosslinking agents have also been used as well as polycarboxylic acids including $C_2$–$C_9$ polycarboxylic acids and citric acid in particular. Crosslinking agents are usually used with a coreactant and/or catalyst. The prior art processes, although differing in specific aspects of crosslinking agents, treated cellulosic fibers with a crosslinking agent, allowed sufficient time for the crosslinking agent to penetrate the fibers, and the fibers were then defibrated into an individualized form by a wide variety of techniques including mechanical defibration as well as various fluffing devices. The fibers were then dried and cured usually in air at elevated temperatures.

Although the above-referred to processes have resulted in the production of acceptable products, nevertheless, particularly for the paper industry a continuing need exists in order to develop crosslinking technology which has the potential of being commercially significant. In particular, it is desired to develop a crosslinking technology which: produces a relatively nit free product at high throughput and low residence time; provides high thermal efficiency and can be conducted in a closed system thereby having no direct atmospheric venting which would provide obvious advantages with regard to health and safety. Ideally, the apparatus will be easily controlled, highly reliable and require only a few moving parts.

SUMMARY OF THE INVENTION

It has now been found that the objects identified above can be achieved in providing individualized crosslinked resilient bulking fibers, as well as from absorbent structures made from said fibers, by utilizing a process wherein cellulosic fibers which have been subjected to conventional wet processing with a crosslinking agent, are dried and cured while suspended in turbulent superheated steam. The chemical crosslinking agent used to treat the fiber prior to drying and curing is applied in an amount sufficient to produce a standard bulk of at least about 3.4 cc/g when incorporated at a level of 15% by weight into British Handsheets according to Tappi Standards but using a pressing pressure of 15 psig. The fibers are introduced into a pressurized dryer where they are entrained in turbulent superheated steam at a pressure of approximately 10 to 70 psia and at an initial steam temperature in excess of about 140° C., preferably from 200° to 300° C. During drying, the temperature may fall to as low as 150° C. but exit temperatures of 170° C. to 220° C. are preferred.

The dried fibers are separated from steam in a conventional cyclone and steam is conducted back for reuse. The fibers separated in said cyclone pass to a fluffer (which may be omitted, if so desired) and then to a curing tube which is similar to the dryer but differs therefrom in that the fibers which enter have a considerably lower water content i.e. they are preferably 100% dry.

For reasons which are not completely understood, it has been found that the water in the fiber unfavorably affects chemical curing because damaging fiber degradation reactions occur at high temperature in the presence of acid and water. Thus, by separating the drying and curing stages and carrying out both under pressurized steam, improve results obtained. The temperatures and pressures of the dryer and curing tube are similar e.g. 140°–350° C. and 10–70 psia, but either can be operated at different temperatures and/or pressures.

It is to be understood that for economic reasons it is preferred to use essentially 100% superheated steam in the pressurized dryer and in the curing tube but any non-oxygen bearing gas could be used as a diluent such as, for example, nitrogen.

In order to perform the drying in a time period that would be acceptable in commercial operations and to minimize the time wherein the fiber is in contact with superheated steam, the dryer temperature must be at least 140° C., but as will be recognized as those skilled in the art, such is merely a poor way of trying to define fiber temperature. It is not the temperature of the dryer which is important (providing it is initially above 140° C.) but the temperature of the fiber, particularly when exiting the dryer. This temperature is difficult to measure but an exit steam temperature of about 150° C. to about 220° C. provides satisfactory results.

It is noted that turbulence provided both in the dryer and curing sections provides internal defibration action, thus, promoting and maintaining a high degree of fiber individualization.

Finally, the fiber is separated from the superheated steam in another cyclone and is thereafter optionally refluffed, pressed and baled or conducted directly to any suitable process involving the use thereof. In some applications, it may be considered desirable to wash the fibers after curing to remove unreacted chemical but, in many applications, this will not be necessary.

It should be noted that it is possible to carry out the separate stages of drying and curing in a single piece of apparatus, but for ease of operation and control, a separate dryer and a separate curing tube are preferred.

DESCRIPTION OF THE PREFERRED EMBODIMENTS

Figure 1:
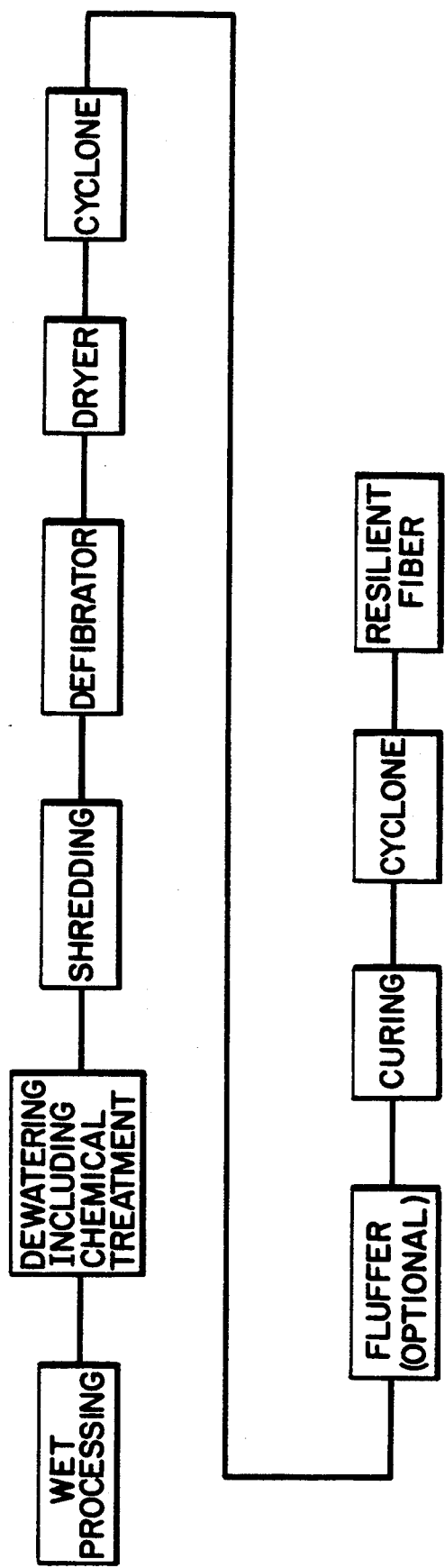
FIG. 1 is a block diagram of the novel process of this invention.

The novel process of this invention can be best understood from the block diagram in FIG. 1 where it is pointed out that wet processing prior to the dryer is conventional technology well known in the art and no novelty is claimed in such technology per se, but only in combination with said curing. Thus, for example, wet processing typically includes formation of a slush fiber, usually at a consistency of about 10-12%, followed by conventional dewatering to a consistency of about 40%, followed by a chemical crosslinking agent treatment step, followed by another conventional dewatering step to bring the consistency back to about 40%, all of these procedures utilizing conventional equipment such as a screw press, repulping, recycling of water with and without chemicals, and recycling of crosslinking agent, if such is desired.

Although any conventional prior art crosslinking agent can be utilized, including those previously mentioned, particular preference is given to 1,3-dimethylol-4,5-dihydroxyimidazolidione (DMDHEU) catalyzed by magnesium chloride. The amount of DMDHEU which is used is approximately 2 to 6% by weight based on the fiber and the amount of magnesium chloride employed is about from 0.5 to 3% by weight. Use of these materials to treat fibers is known in the art as is evidenced from U.S. Pat. No. 3,440,135, the entire disclosure of which is incorporated by reference. The process of the present invention is also well suited to be used with polycarboxylic acid crosslinkers such as citric acid, catalyzed with sodium hypophosphite or monosodium phosphate as well 1,3-dimethyl-4,5-dihydroxyethyleneurea (DHDMEU) which is also catalyzed with magnesium chloride. Use of the citric acid is described in said U.S. Pat. No. 5,137,537 as well as European published application 440,472, published Aug. 7, 1992.

When the fibers are being impregnated with a crosslinking agent, the impregnated fibers are generally held in an equilibration chest for a sufficient amount of time to allow the crosslinking agent to thoroughly impregnate the fibers. The impregnated fibers are subsequently subjected to conventional dewatering operations and then passed through a conventional shredder and a conventional defibrator. As previously indicated, all these techniques are well known in the art and no novelty per se is claimed in any of them.

The novel process of this invention really begins when cellulosic fibers, usually at a consistency of about 20 to 50 wt. %, are introduced into the dryer. The dryer is a pressurized dryer disclosed in both U.S. Pat. No. 4,043,049 and U.S. Pat. No. 4,244,778, the entire disclosure of both being incorporated by reference. As has heretofore been pointed out, the dryer is a pressurized dryer operating with superheated steam at a pressure of approximately 10-70 psia and a entrance steam temperature in excess of about 140° C. and less than 300° C. preferably from 200° to 300° C.

The dryer of U.S. Pat. No. 4,244,778 is of the type which provide turbulent flow thereby entraining the fibers in said superheated steam.

Dried heated fiber is separated from the steam in a conventional cyclone, and the steam can be recycled back to the dryer or any other part of the process as desired.

The fiber separated in the cyclone passes into a conventional fluffer (which may be omitted if so desired) and into a curing tube which is of generally the same configuration as the dryer. As mentioned previously, if desired the crosslinked fibers may be washed to remove unreacted chemical crosslinking agent although in many cases the fibers may be used without washing.

A particularly advantageous aspect of utilizing the novel process of this invention is that the formation of nits and knots is considerably reduced as compared to techniques not involving drying and cure while entrained in a stream of turbulent superheated steam. As is known in the art, the formation of nits and knots is a common problem in the preparation of resilient bulking fibers especially when chemical crosslinking is employed.

It has been common practice in the art to employ debonding agents, mechanical defibration such as hammer milling and screening to reduce the nit/knot content of the treated fibers. Such measures tend to be costly and can be deleterious to the fiber and paper quality. The novel process of this invention reduces the amounts of nits and knots and thereby provides additional economic benefits.

The novel process of this invention is applicable to dry lap or never-dried wood fibers. Any at least partially chemically digested wood pulp fiber may be used. Bleached high- or low-brightness pulps may be used. We prefer kraft pulps, ideally high brightness kraft softwood pulps, but either hardwood or softwoods pulped using the kraft, sulfite, soda cook, and modifications of these processes may be used. Throughout this specification and claims, the term "fibers" should understood to comprehend both the relatively high aspect ratio particles typically referred to as fibers as well as the lower aspect ratio particles and fiber debris often referred to as fines.

The process of this invention is not limited to wood pulp fibers but is applicable to fibers such as bagasse, kenaf, abaca, bamboo, sisal, cotton and other individualized non-wood cellulosic fibers.

The cured fibers thus prepared can then be dispersed for use. Preferably, the dispersion step involves contacting the cured fibers with water or preferably with a foamed furnish. These bulking fibers may then be used—alone or in blends—to prepare products that exhibit improved bulking and absorbent properties. The improvement in absorbency relates both to faster rate of absorbency and to increased fluid-holding capacity. The amounts of crosslinked fibers used to prepare the products are readily determinable by those skilled in the art. For instance, filtration and absorbent product applications will often be made 100% from the fibers of the present invention. On the other hand, towel and tissue paper products may be made by blending fibers according to the present invention with a majority of conventional wood pulp fibers. In such applications, crosslinked fibers may be used in an amount of about 30% or less, preferably about 15% by weight of the paper product.

Figure 2:
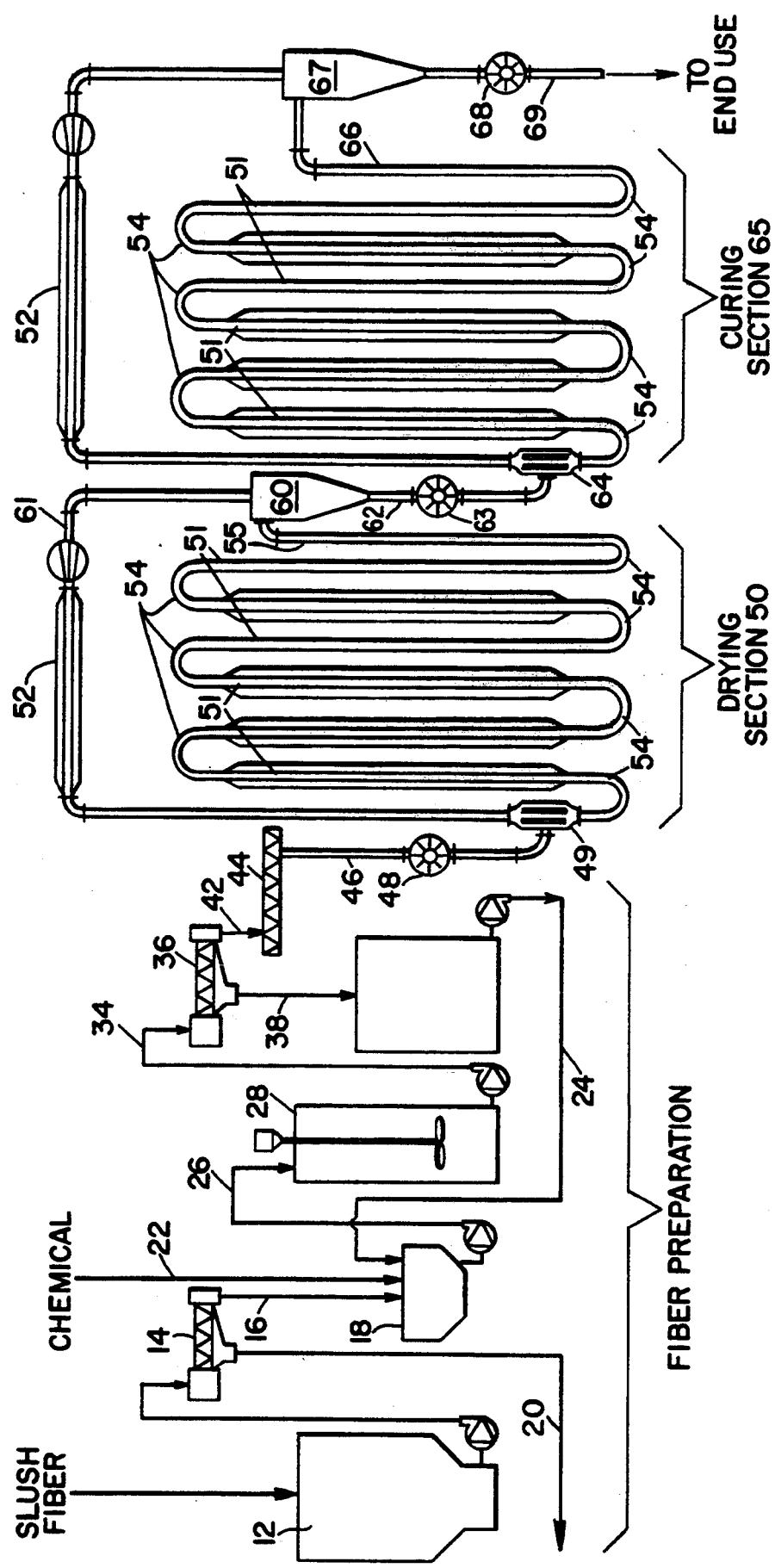
FIG. 2 is a schematic of the novel process of this invention.

FIG. 2 illustrates the complete process of this invention in that a slush fiber at a consistency of about 10–12% is stored in chest 12 which is conducted to screw press 14 and dewatered so that the consistency is at least 40 wt % solids. Dewatered fiber leaves line 16 and is conducted to repulper 18. Reject water is conducted through line 20 and may be discharged or used in other places in the plant environment. The crosslinking agent and catalyst are introduced through line 22, while makeup water bearing catalyst and crosslinking agent not previously absorbed is introduced through line 24. The pulp impregnated with crosslinking agent at a consistency of 1–40%, preferably 4–12 wt %, more preferably 6–8 wt %, is conducted through line 26 to equilibration chest 28. Equilibration is an optional step which is normally used to ensure more effective utilization of crosslinking agent by allowing sufficient time for thorough impregnation of the fibers. When equilibration chest 28 is used, it is maintained at relatively low agitation to allow the fiber to become thoroughly impregnated with the crosslinking chemicals. Treated fiber from equilibration chest 28 passes through line 34 and is conducted to screw press 36. Water and chemicals rejected in screw press 36 are recycled through line 38. The fibers from screw press 36 are conducted through line 42 to a shredding conveyer 44 and thence through line 46 to rotary feed valve 48 and a defibrator 49 into pressurized dryer 50.

Pressurized dryer 50 is of the type disclosed in U.S. Pat. No. 4,244,778 and 4,043,049, the entire disclosure of both being herein incorporated by reference. As can be seen, pressurized dryer 50 comprises a long tortuous partially steam-jacketed tube 51 having numerous bends 54 formed therein. As disclosed in said U.S. Pat. No. 4,244,778, a turbulent flow is created which entrains the fibers and leads to additional fiber individualization and/or fluffing.

The dried fiber exits through line 55 into cyclone 60 wherein steam can be recycled through line 61. Fiber which is separated in cyclone 60 passes through line 62 to the curing section 65 via rotary valve 63 and fluffer 64 (optional). Curing section 65 is substantially identical to dryer 50 and is of substantially the same construction as the equipment disclosed in U.S. Pat. No. 4,244,778, except that the materials used must be capable of withstanding the higher temperatures involved in the practice of the present invention. Flow through the curing tube provides turbulence which entrains the fiber in superheated steam.

The fiber is then led via line 66 into cyclone 67 wherein the fiber is separated from the superheated steam. The fiber exiting through rotary valve 68 and line 69 is thereafter optionally washed, refluffed, pressed and/or baled or conducted directly to further processing operations.

Superheaters 52 are, in both drying and curing sections, used to boost temperatures to bring the incoming fiber up to operating temperatures quickly.

Although a screw press is depicted for dewatering, it is obvious that other equipment can be used which performs a similar function such as a twin roll or belt press. Similarly, where we have indicated a shredding conveyor, a simple screw conveyor, belt conveyor or similar apparatus can be used. In some cases, it may be advantageous to use an inclined wire or other dewatering equipment, such as a centrifuge, to impart a two-dimensional structure to the dewatered fiber.

The following examples will now illustrate the best mode contemplated for carrying out the invention.

In the examples which follow, the process described in FIG. 2 was used with various pulps with crosslinking agent as indicated. The temperature of the superheated steam in the dryer when the fiber entered through line 46 was about 250° C. and it dropped to about 190° C. when the fiber exited through line 55. The temperature of the superheated steam in the curing tube was about 350° C. when the fiber entered through line 62 and it dropped to about 200° C. when it exited through line 66. The dryer operated at a pressure of about 20–25 psia and the curing tube pressure was about 20–25 psia. Had lower dryer temperatures been used, it would have been desirable to use higher temperatures for the superheated steam in the curing section. In some cases, the higher curing temperature would have been detrimental to fiber quality. In each of the examples, 15 wt. % of the fiber produced was blended with 85 wt. % of a control furnish and pressed into British handsheets according to Tappi standard methods except that a pressing pressure of 15 psig was used. Bulk, breaking length and brightness were measured and compared to handsheets made from said control furnish. Throughout this specification and claims, the term "standard bulk" should be understood to comprehend the bulk of a handsheet formed as described in this paragraph. The typical control furnish and the properties of handsheets made therefrom is listed below

| CONTROL FURNISH | | |
|---|---|---|
| Compositions | | |
| 50 wt. % Previously-dried Softwood Kraft | | |
| 50 wt. % Never-dried Northern Hardwood Kraft | | |
| Properties | | |
| (All measured at 400 Canadian Standard Freeness (CSF) | | |
| Bulk cc/g | B.L.[1] km | Brite[2] % |
| 2.4 | 4.4 | 85.6 |

[1]Breaking length
[2]% Brightness as determined by a G. E. brightness meter

EXAMPLES 1–3

These examples will illustrate the novel process of this invention when citric acid catalyzed by sodium hypophosphite is used as a crosslinking agent.

EXAMPLE 1

Never-dried hardwood Kraft fibers were treated with a solution of citric acid and sodium hypophosphite in accordance with the process described in FIG. 2 to produce fiber having 4.1 wt % citric acid and 1.4 wt % sodium hypophosphite in/on the fiber based on dry weight of the fiber. Handsheets obtained by blending 15 wt. % of the fiber had the properties listed below:

| Bulk cc/g | B. L. km | Brite % |
|---|---|---|
| 3.3 | 3.8 | 77.2 |

EXAMPLE 2

Dry lap softwood Kraft fibers were treated with a solution of citric acid and sodium hypophosphite in accordance with the process described in FIG. 2 to produce fiber having 5.0 wt % citric acid and 3.9 wt % sodium hypophosphite in/on the fiber based on the dry weight of the fiber. Handsheets obtained by blending 15 wt. % of the fiber had the properties listed below:

| Bulk cc/g | B. L. km | Brite % |
|---|---|---|
| 3.5 | 3.4 | 81.2 |

EXAMPLE 3

Never-dried softwood Kraft fibers were treated with a solution of citric acid and sodium hypophosphite in accordance with the process described in FIG. 2 to produce fiber having 4.9 wt % citric acid and 1.3 wt % sodium hypophosphite in/on the fiber based on the dry weight of the fiber. Handsheets obtained by blending 15 wt. % of the fiber had the properties listed below:

| Bulk cc/g | B. L. km | Brite % |
|---|---|---|
| 3.6 | 3.4 | 77.0 |

EXAMPLES 4–9

These examples will illustrate the novel process of this invention when 1,3-dimethyl-4,5-dihydroxyimidazolidione (DMDHEU) catalyzed by magnesium chloride is used as a crosslinking agent.

EXAMPLE 4

Never-dried softwood Kraft fibers were treated with a solution of DMDHEU and magnesium chloride in accordance with the procedure of FIG. 2 to produce fiber having 3.0 wt % DMDHEU and 0.3 wt % magnesium chloride in/on the fiber based on the dry weight of the fiber. Handsheets obtained by blending 15 wt. % of the fiber had the properties listed below:

| Bulk cc/g | B. L. km | Brite % |
|---|---|---|
| 4.3 | 3.2 | 80.8 |

EXAMPLE 5

Never-dried softwood Kraft fibers were treated with a solution of DMDHEU and magnesium chloride in accordance with the procedure of FIG. 2 to produce fiber having 3.0 wt % DMDHEU and 0.3 wt % magnesium chloride in/on the fiber based on the dry weight of the fiber. Handsheets obtained by blending 15 wt. % of the fiber had the properties listed below:

| Bulk cc/g | B. L. km | Brite % |
|---|---|---|
| 4.1 | 3.1 | 82.8 |

EXAMPLES 6–11

Examples 6–11 illustrate the novel process of this invention when citric acid catalyzed with sodium monophosphate is used as the crosslinking agent.

EXAMPLE 6

Previously dried softwood Kraft fibers were treated with a solution of citric acid and sodium monophosphate in accordance with the process described in FIG. 2 to produce fiber having 5.0 wt % citric acid and 3.9 wt % sodium monophosphate in/on the fiber based on dry weight of the fiber. Handsheets obtained by blending 15 wt. % of the fiber had the properties listed below:

| Bulk cc/g | B. L. km | Brite % |
|---|---|---|
| 3.5 | 3.4 | 81.2 |

EXAMPLE 7

Never-dried softwood Kraft fibers were treated with a solution of citric acid and sodium monophosphate in accordance with the process described in FIG. 2 to produce fiber having 6.8 wt % citric acid and 5.1 wt % sodium monophosphate in/on the fiber based on dry weight of the fiber. Handsheets obtained by blending 15 wt. % of the fiber had the properties listed below:

| Bulk cc/g | B. L. km | Brite % |
|---|---|---|
| 3.4 | 3.2 | 82.0 |

EXAMPLE 8

Never-dried softwood Kraft fibers were treated with a solution of citric acid and sodium monophosphate in accordance with the process described in FIG. 2 to produce fiber having 3.7 wt % citric acid and 3.4 wt % sodium monophosphate in/on the fiber based on dry weight of the fiber. Handsheets obtained by blending 15 wt. % of the fiber had the properties listed below:

| Bulk cc/g | B. L. km | Brite % |
|---|---|---|
| 3.4 | 3.1 | 82.0 |

EXAMPLE 9

Secondary fibers were treated with a solution of citric acid and sodium monophosphate in accordance with the process described in FIG. 2 to produce fiber having 4.1 wt % citric acid and 3.0 wt % sodium monophosphate in/on the fiber based on dry weight of the fiber. Handsheets obtained by blending 15 wt. % of the fiber had the properties listed below:

| Bulk cc/g | B. L. km | Brite % |
|---|---|---|
| 3.0 | 3.5 | 80.4 |

EXAMPLE 10

Never-dried softwood Kraft fibers were treated with a solution of citric acid and sodium monophosphate in accordance with the process described in FIG. 2 to produce fiber having 5.7 wt % citric acid and 1.2 wt % sodium monophosphate in/on the fiber based on dry weight of the fiber. Handsheets obtained by blending 15 wt. % of the fiber had the properties listed below:

| Bulk cc/g | B. L. km | Brite % |
|---|---|---|
| 4.0 | 3.0 | 83.1 |

EXAMPLE 11

The process of Example 10 was repeated with the exception that the fiber was not cured in turbulent superheated steam. In this example, the fiber exiting the cyclone from the pressurized dryer was mechanically fluffed, made into a handsheet and cured by passing 190° C. air through the sheet for 40 seconds. The handsheets had the properties listed below:

| Bulk cc/g | B. L. km | Brite % |
|---|---|---|
| 4.3 | 3.1 | 82.1 |

As can be seen a lower brightness value was obtained as compared to Example 10.

What is claimed is:

1. In a method for preparing crosslinked cellulosic fibers wherein said fibers are treated with a chemical crosslinking agent, individualized, dried and cured, the improvement which comprises carrying out the drying and the curing in two separate stages, wherein
   a) the drying is carried out in a pressurized vessel providing turbulent flow so as to entrain said treated fibers in superheated steam, said drying being carried out with pressurized steam at an initial temperature ranging from about 140° to about 350° C. and a pressure of 10–105 psia;
   b) separating said steam from said fibers; and
   c) curing said treated fibers in a pressurized vessel providing turbulent flow so as to entrain said treated fibers in superheated steam and render them anfractuous, said curing being carried out with pressurized steam at an initial temperature ranging from about 140°–350° C. at a pressure of 10 to 105 psia.

2. The process of claim 1 wherein said pressurized steam in steps a) and c) is essentially 100% superheated steam.

3. The process of claim 2 wherein step a) is carried out at a temperature of from 200° C. to 300° C.

4. The process of claim 3 wherein step a) is carried out at a pressure of from 20 to 90 psia.

5. The process of claim 2 wherein step c) is carried out at a pressure of from 20 to 90 psia.

6. The process of claim 5 wherein step c) is carried out at a temperature of from 200° to 300° C.

7. The process of claim 1 wherein said chemical crosslinking agent used to treat the fiber prior to drying and curing is applied in an amount sufficient to produce a standard bulk of at least about 3.4 cc/g when incorporated into British Handsheets when incorporated at a level of 15% by weight according to Tappi Standards but using a pressing pressure of 15 psig.

8. The process of claim 7 wherein the crosslinking agent is citric acid.

9. The process of claim 7 wherein the crosslinking agent is 1,3-dimethyl-4,5-dihydroxyimidazolidione.

10. The process of claim 7 wherein the crosslinking agent is 1,3-dimethyl-4,5-dihydroxyethyleneurea.

11. The process of claim 8 wherein a catalyst or coreactant is used.

12. The process of claim 9 wherein a catalyst or coreactant is used.

13. The process of claim 10 wherein a catalyst or coreactant is used.

14. The process of claim 11 wherein said catalyst or coreactant is sodium hypophosphite.

15. The process of claim 12 wherein said catalyst or coreactant is magnesium chloride.

16. The process of claim 13 wherein said catalyst or coreactant is magnesium chloride.

* * * * *